United States Patent [19]

Mays

[11] Patent Number: 5,409,377
[45] Date of Patent: Apr. 25, 1995

[54] DENTAL POST STORAGE AND MOUNTING DEVICE

[76] Inventor: Ralph C. Mays, 10322 B E. 58th St., Tulsa, Okla. 74146

[21] Appl. No.: 194,844

[22] Filed: Feb. 14, 1994

[51] Int. Cl.⁶ .............................................. A61C 5/08
[52] U.S. Cl. .................................... 433/220; 206/368
[58] Field of Search ............... 433/173, 174, 175, 220, 433/221, 225; 206/63.5, 368

[56] References Cited

U.S. PATENT DOCUMENTS

| | | | |
|---|---|---|---|
| 3,378,925 | 4/1968 | Faller | 433/26 |
| 3,579,306 | 5/1971 | Crane . | |
| 3,703,977 | 11/1972 | Pisarek | 206/63.5 |
| 3,890,204 | 6/1975 | Avery . | |
| 4,220,712 | 9/1980 | Staffolani | 433/173 |
| 4,364,473 | 12/1982 | Bogaert | 206/63.5 |
| 4,445,611 | 5/1984 | Shofu | 206/380 |
| 4,856,648 | 8/1989 | Krueger | 206/63.5 |
| 5,062,800 | 11/1991 | Niznick | 433/173 |
| 5,236,361 | 8/1993 | Mays | 433/221 |

FOREIGN PATENT DOCUMENTS 427181 8/1911 France .
2421990 11/1975 Germany .

*Primary Examiner*—Cary E. O'Connor
*Attorney, Agent, or Firm*—Head & Johnson

[57] ABSTRACT

A combined storage container and installation device for a dental post having an elongated distal end and a proximal head. The device includes an elongated container having a top opening, a cap has a recess therein to hold the proximal head in the recess while allowing fluid to pass into and through the recess. The cap is received and held in the open top of the container. By holding and manipulating the cap, the dental post may be removed from the container and installed under sterilized conditions.

17 Claims, 1 Drawing Sheet

DENTAL POST STORAGE AND MOUNTING DEVICE

BACKGROUND OF THE INVENTION

1. Field of the Invention

The present invention relates to a combined storage and installation device for a dental post. In particular, the present invention relates to a container to receive and hold a dental post wherein the dental post may be subsequently removed from the container and installed in a patient without contamination.

2. Prior Art

Dental posts are widely used for securing a dental device, such as a crown or the like, to a tooth. In certain instances, the human tooth is chipped or worn away so that the crown is difficult to secure to the natural tooth. To securely support a dental device, such as a crown, onto a natural tooth, a pin or post is embedded into an opening made in the tooth so that a portion of the pin or post extends externally from the tooth and serves as reinforcement for receiving a crown.

In mounting a dental post into a natural tooth, a dentist bores a hole of selected diameter generally following the tooth's root canal. The bore hole is drilled from the tooth's external surface into the tooth. The dental post is thereafter inserted into the hole.

Contamination of the dental post can quickly lead to infection. Additionally, some types of dental posts have a composite material on the stem; touching or handling of the dental post decreases the integrity of the dental post. As an example, oil from human fingers on the surface of the post decreases the ability to bond the tooth.

The dental post must be packaged and transported under sterile conditions and then installed in the patient under sterile conditions. Alternatively, the dental post may be sterilized immediately prior to installation in the tooth.

Various types of packaging have been used in the past for dental posts. As an example, Krueger, U.S. Pat. No. 4,856,648, identifies the problem of possible contamination. Krueger recesses a socket in the head of the dental post to secure a cap thereto. This arrangement requires a special dental post with a recessed socket. Additionally, the socket itself is not sterilized with the cap inserted.

There remains a need for a combined storage container to retain and store standard dental posts and to also be used as an installation device when installing in a patient.

It is, therefore, a principal object and purpose of the present invention to provide a combined storage container to hold and store a dental post and allow sterilization of the dental post without handling or contamination of the dental post.

It is a further object and purpose of the present invention to provide a combined storage and sterilization container which will allow sterilization of the entire dental post.

It is a further object and purpose of the present invention to provide a cap which acts as a handle to retain, move and install the dental post.

SUMMARY OF THE INVENTION

The present invention provides a combined storage and container and installation device for a dental post. A dental post, including an elongated distal end and a proximal head, may be stored within the container of the device. The elongated container, which receives the entire dental post therein, includes a top opening larger than the diameter of the dental post. The interior diameter of the container is at all places larger than the diameter of the dental post.

A somewhat elongated cap has a recess at one end. The recess is slightly tapered so that its widest point is at the surface of the cap. The recess receives and holds the proximal head of the dental post by frictional engagement. When the cap is engaged over the proximal head, the axis of the cap is aligned with the axis of the dental post.

The cap is, in turn, receivable in the top opening of the container. The exterior of the cap engages the interior wall of the container so that the cap is retained in the open top of the container. An externally extending flange on the cap acts as a stop to prohibit the cap from being inserted past a pre-determined point.

In one embodiment, the proximal head of the dental post does not form a seal with the recess of the cap. Accordingly, while the dental post may be wedged and retained in the cap recess, fluid will be able to pass into and through the recess.

In order to utilize the device, initially the distal end of the dental post is inserted and received within the recess of the cap. Thereafter, movement or manipulation of the cap will move or manipulate the dental post.

The sterilization process may then be performed through any known process.

The cap and accompanying dental post are placed into the container through the open top with the distal end inserted first into the container. The cap is then wedged into the opening of the top of the container so that the dental post is thereby suspended inside the container.

The dental post may be sterilized using any known sterilization procedure. Gamma ray sterilization may be performed while the post is in the container. Gas, steam or other fluid may be used to surround the device and pass through the additional opening. Additionally, fluid will be allowed to move into and through the recess in the cap in order to sterilize the post.

The dental post may be stored and transported in the container without contamination until the dental post is ready for insertion in a patient. The cap and accompanying post are then separated from the container by moving the cap in an opposite direction from the elongated container. The dental post is thus moved and manipulated without touching or otherwise contaminating the dental post.

Thereafter, the dental post is inserted into a pre-arranged or pre-drilled opening in a tooth. Again, the cap securely holds the dental post so that moving the cap will also translate to movement of the dental post. Finally, once the dental post is secured within the opening in the tooth, the cap may be separated from the dental post. While holding the exterior of the cap, the axis of the cap will be brought out of alignment with the axis of the dental post. The frictional engagement between the proximal head and the recess will thereby be broken. The entire installation procedure is, thus, performed without handling or touching of the dental post.

DETAILED DESCRIPTION OF THE PREFERRED EMBODIMENTS

Figure 1:
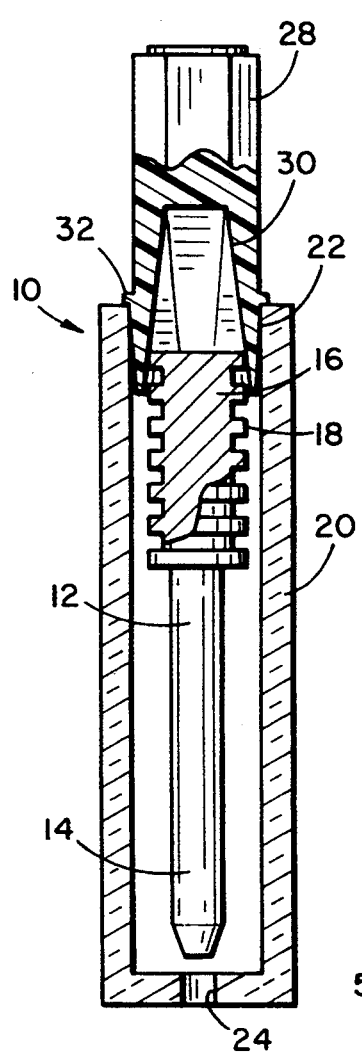
FIG. 1 illustrates a combined storage and sterilization container and installation device for a dental post constructed in accordance with the present invention which is partially cut-away to reveal the dental post held therein.
Figure 3:
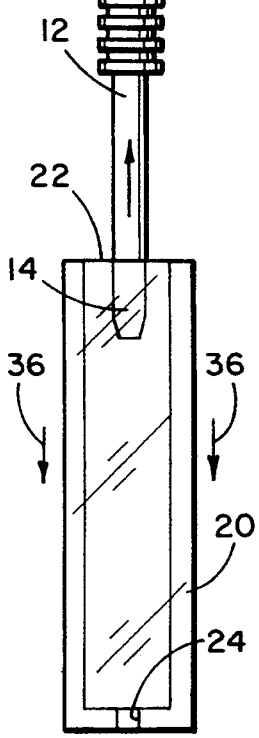

Referring to the drawings in detail, FIG. 1 shows a combined storage container and installation device 10 of the present invention partially cut-away. A dental post 12, partially cut away, is stored within the combined device 10 shown in FIG. 1. The dental post 12 includes an elongated distal end 14 and a proximal head 16. After installation in a patient, the distal end is embedded in an opening which is drilled into a tooth while the proximal head extends therefrom. The proximal head is thereafter used to secure to a crown or other dental device.

The dental post 12 of the present embodiment includes a series of extending parallel flanges 18 at the head 16. It will be recognized that dental posts of other configurations might be utilized with the present invention.

An elongated container 20 receives the entire dental post 12 therein. The elongated container is, thus, longer than the length of the dental post. The elongated container 20 includes a top opening 22 larger than the diameter of the dental post 12. In the present embodiment, the container 20 also includes an additional opening 24 opposed to the top opening. As will be seen herein, the interior diameter of the container 20 is at all places larger than the diameter of the dental post 12 so that the dental post does not touch the interior of the container.

A cap 28 is received in the open top 22. The caps may be colored coded to identify different size posts. In FIG. 1, the cap 28 is partially cut away for clarity. The cap 28 is somewhat elongated and has a recess 30 at one end. The recess 30 is slightly tapered so that its widest point is at the surface of the cap 28. In the present embodiment, the recess is tapered at approximately 7°. The recess receives and holds the proximal head 16 of the dental post by frictional engagement. When the cap is engaged over the proximal head, the axis of the cap 28 is aligned with the axis of the dental post 12.

The cap 28 is, in turn, receivable in the top opening 22 of the container as seen in FIG. 1.

The exterior of the cap 28 engages the top opening of the container 20 so that the cap is retained in the open top 22 of the container. An externally extending flange 32 acts as a stop to prohibit the cap 28 from being inserted into the container past a certain maximum point.

Figure 2:
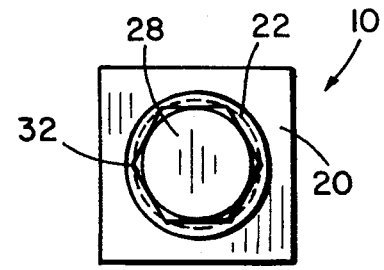
FIG. 2 is a top plan view of the combination device shown in FIG. 1.

With reference to the top plan view shown in FIG. 2 and continuing reference to FIG. 1, it will be observed that while the proximal head 14 is substantially cylindrical, the cap recess 30 is neither cylindrical nor frusto-conical. The recess has flat walls so that the recess is square in cross-section. The proximal head does not, thus, form a seal with the recess. Accordingly, while the dental post 12 may be wedged and retained in the recess, fluid will be able to pass into and through the recess.

Alternatively, the recess might be frusto-conical.

FIG. 2 illustrates a top plan view of the device. FIGS. 1, 3, 4 and 5 illustrate a typical sequential procedure to store a dental post and thereafter install the dental post in a patient. Initially, the distal end of the dental post is inserted and received within the recess 30 of the cap 28. Once the proximal head is inserted in the recess, movement or manipulation of the cap will move or manipulate the dental post.

The dental post may be sterilized using known sterilization procedures such as gamma ray sterilization while the post is in the container. Alternatively, the cap and post may be removed from the container. Gas, steam or other is in fluid will be allowed to surround the post. Accordingly, the fluid will surround and move past the dental post 12. Additionally, fluid will be allowed to move into and through the recess 30 in the cap. In this manner, the entire dental post may be sterilized.

As seen in FIG. 1, the cap and dental post are then placed into the container through the open top 22. The distal end 14 is inserted first into the container. The cap 28 then wedges into the open top 22 of the container. It will be observed that the dental post is thereby suspended within the container.

Once the dental post is ready for insertion in a patient, the cap is then separated from the container by moving the cap in an opposite direction from the elongated container 20 as illustrated by arrows 34 and 36. This may be accomplished by grasping in one hand the end of the cap at arrows 38 while grasping the container in the other hand. It will be observed that the dental post 12 is thus moved and manipulated without touching or otherwise contaminating the dental post.

Figure 4:
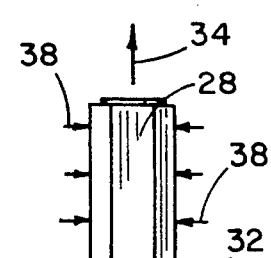
FIGS. 3, 4, and 5 illustrate sequentially the process to remove a dental post from the combined device of the present invention and to install it in a patient's tooth.
Figure 4:
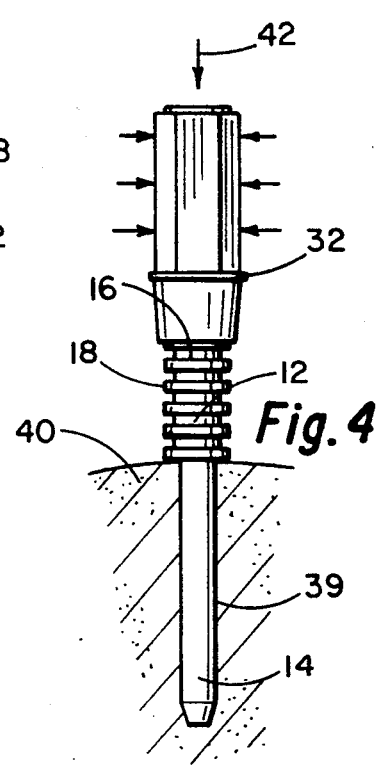

Thereafter, as shown in FIG. 4, the dental post is inserted into a prearranged or pre-drilled opening 39 in a tooth 40. Arrow 42 indicates the movement of the cap. Again, the cap securely holds the dental post so that moving the cap will translate to movement of the dental post.

Figure 5:
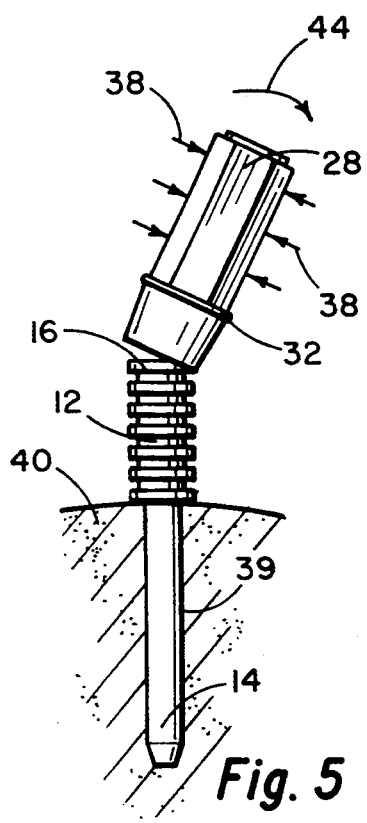

Finally, as seen in FIG. 5, once the dental post is secured within the tooth opening 38, the cap 28 may be separated from the dental post. While holding the cap 28 at arrows 38, the axis of the cap will be brought out of alignment with the axis of the dental post 12, as best illustrated by arrow 44 in FIG. 5. The entire installation procedure has, thus, been performed without handling or touching of the dental post.

Figure 6:
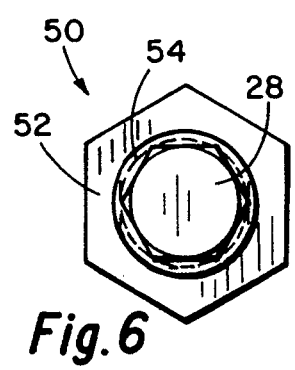
FIG. 6 is a top plan view of an alternate embodiment of the combined storage and sterilization container and installation device constructed in accordance with the present invention.

FIG. 6 illustrates a top plan view of an alternate embodiment of the combined device 50. The exterior of the container 52 is hexagon in cross-section rather than square. While the exterior of the container may take other shapes, a noncylindrical shape has been found advantageous to prevent the container 20 from rolling if placed on its side. The opened top of container 52 is indicated by the numeral 54.

Whereas, the present invention has been described in relation to the drawings attached hereto, it should be understood that other and further modifications, apart from those shown or suggested herein, may be made within the spirit and scope of this invention.

What is claimed is:

1. A combined storage container and installation device for a dental post having an elongated distal end and a proximal head, the distal end being receivable in a drilled hole in a tooth in the mouth of a patient, which device comprises:

an elongated container to receive the dental post therein, said container having a top opening;

a cap having a recess configured and dimensioned to receive and releasably hold said proximal head of said dental post, said cap being receivable in said top opening for storage of said dental post in said elongated container, said cap being configured and dimensioned to be manually manipulatable in the mouth of a patient so that said dental post may be removed from said container and installed in a patient while holding said cap and without touching said dental post, said cap being detachable from said dental post by pivotation of said cap relative to said dental post with substantially no pulling action between said cap and said dental post being required.

2. A device as set forth in claim 1 wherein said proximal head is substantially cylindrical and said cap recess is neither cylindrical nor frusto-conical in order to allow fluid to pass into and through said recess while said proximal head is held therein.

3. A device as set forth in claim 1 wherein said dental post may be sterilized while in said container.

4. A device as set forth in claim 1 wherein said elongated container has an interior larger in diameter than the diameter of said dental post.

5. A device as set forth in claim 1 wherein said cap recess is tapered.

6. A device as set forth in claim 5 wherein said recess is tapered at approximately 7°.

7. A combined device as set forth in claim 1 including at least one additional opening in said container to allow fluid to pass into and through said container.

8. A combined device as set forth in claim 1 wherein the axis of said dental post and the axis of said cap are aligned during installation and wherein said cap is moved out of alignment to separate said dental post from said cap.

9. A combined storage and sterilization container and installation device for a dental post having an elongated distal end and a proximal head, which device comprises:

an elongated container having a top opening;

a cap removably receivable in said container top opening and having a recess therein;

means to receive and hold said proximal head in said cap recess while allowing sterilizing fluid to pass into said recess to thereby surround said dental post proximal head; and means to install said dental post by holding and manipulating said cap in order to install said dental post under sterilized conditions.

10. A combined device as set forth in claim 9 including means to allow sterilizing fluid to pass into and through said container and into said recess in said cap while said cap is in said container top opening.

11. A combined device as set forth in claim 10 wherein said proximal head is substantially cylindrical and said cap recess is neither cylindrical nor frusto-conical.

12. A combined device as set forth in claim 9 wherein said means allowing sterilizing fluid to pass into said recess in said cap includes said recess not being circular and said dental post being cylindrical.

13. A combined device as set forth in claim 9 wherein said cap recess is tapered.

14. A combined device as set forth in claim 12 wherein said cap recess is tapered at approximately 7°.

15. A method of storing, sterilizing, and installing a dental post having an elongated distal end and a proximal head, which method comprises:

receiving and holding said proximal head in a recess in a cap, the recess being configured to permit the flow of sterilizing fluid therein while holding said post proximal head;

inserting said cap and dental post in an elongated container;

receiving and holding said cap in an open top in said container, said container having an aperture therein;

sterilizing said dental post by passing sterilizing fluid into said container and into said recess so that thereby said sterilizing fluid surrounds the entirety of said dental post including said proximal head;

removing said dental post from said container by holding and manipulating said cap; and installing said dental post in said patient without touching said dental post.

16. A method of storing, sterilizing and installing a dental post according to claim 15 wherein said last mentioned step of installing said dental post in said patient without touching said dental post includes the step of detaching said cap from said dental post by pivotation of said cap relative to said dental post with substantially no pulling action between said cap and said dental post.

17. A method of storing and installing a dental post into a drilled hole in a tooth in the mouth of a patient, the dental post having an elongated distal end and a proximal head, which method comprises:

receiving and holding said proximal head in a tapered recess in a cap, the cap being configured and dimensioned to be manually manipulatable in the mouth of a patient;

inserting said cap and dental post in the open top of an elongated container for shipment and/or storage;

removing said dental post from said container by holding and manipulating said cap; and installing said dental post in a drilled hole in a tooth in the mouth of a patient by manually manipulating said cap without handling said dental post, said cap then being detachable from said dental post by pivotation of said cap relative to said dental post with substantially no pulling action between said cap and said dental post being required.

* * * * *